United States Patent
Sadasivan Vijayakumari et al.

(10) Patent No.: US 10,239,013 B2
(45) Date of Patent: Mar. 26, 2019

(54) PROCESS FOR RECOVERING METHANE FROM A GAS STREAM COMPRISING METHANE AND ETHYLENE

(71) Applicant: SHELL OIL COMPANY, Houston, TX (US)

(72) Inventors: Sivakumar Sadasivan Vijayakumari, Gonzales, LA (US); Charles-Edouard Sanders, Gyeongsangnam-do (KR); Vatsal Mukundlal Shah, Sugar Land, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/305,523

(22) PCT Filed: Apr. 20, 2015

(86) PCT No.: PCT/EP2015/058510
§ 371 (c)(1),
(2) Date: Oct. 20, 2016

(87) PCT Pub. No.: WO2015/162090
PCT Pub. Date: Oct. 29, 2015

(65) Prior Publication Data
US 2017/0087501 A1    Mar. 30, 2017

(30) Foreign Application Priority Data
Apr. 22, 2014 (EP) .................................... 14165492

(51) Int. Cl.
*B01D 53/047* (2006.01)
*C07C 7/12* (2006.01)
(Continued)

(52) U.S. Cl.
CPC ............ *B01D 53/047* (2013.01); *C07C 7/005* (2013.01); *C07C 7/04* (2013.01); *C07C 7/12* (2013.01);
(Continued)

(58) Field of Classification Search
None
See application file for complete search history.

(56) References Cited

U.S. PATENT DOCUMENTS

| 5,025,108 A | 6/1991 | Cameron et al. |
| 5,113,032 A | 5/1992 | Cameron et al. |

(Continued)

FOREIGN PATENT DOCUMENTS

| CA | 1199881 | 1/1986 |
| DE | 969431 | 6/1958 |
| WO | 2009105251 | 8/2009 |

OTHER PUBLICATIONS

International Search Report dated Jul. 21, 2015 for PCT/EP2015/058510 filed Apr. 20, 2015.

*Primary Examiner* — Tam M Nguyen

(57) ABSTRACT

The invention relates to a process for recovering methane from a gas stream comprising methane and ethylene, comprising a sorption step which comprises contacting the gas stream comprising methane and ethylene with a sorption agent which has a lower affinity for methane than for ethylene, resulting in sorption of ethylene and 0 to 90% of the methane by the sorption agent and in a gas stream comprising methane in an amount of 10 to 100% based on the amount of methane in the gas stream that is subjected to the sorption step; and a desorption step which comprises desorbing sorbed ethylene and optionally sorbed methane resulting in a gas stream comprising ethylene and optionally methane.

10 Claims, 1 Drawing Sheet

(51) Int. Cl.
*C07C 7/05* (2006.01)
*C07C 7/04* (2006.01)
*C07C 7/00* (2006.01)

(52) U.S. Cl.
CPC .. *B01D 2253/102* (2013.01); *B01D 2253/108* (2013.01); *B01D 2256/245* (2013.01); *B01D 2257/102* (2013.01); *B01D 2257/108* (2013.01); *B01D 2257/502* (2013.01); *B01D 2257/504* (2013.01); *B01D 2257/7022* (2013.01); *Y02C 10/08* (2013.01); *Y02P 20/152* (2015.11); *Y02P 20/51* (2015.11)

(56) References Cited

U.S. PATENT DOCUMENTS

| | | |
|---|---|---|
| 8,192,709 B2 | 6/2012 | Reyes et al. |
| 2002/0007101 A1 | 1/2002 | Senetar et al. |
| 2015/0307415 A1* | 10/2015 | Rafique .................... C07C 2/84 |
| | | 518/703 |

* cited by examiner

PROCESS FOR RECOVERING METHANE FROM A GAS STREAM COMPRISING METHANE AND ETHYLENE

PRIORITY CLAIM

The present application is a National Stage (§ 371) application of PCT/EP2015/058510, filed 20 Apr. 2015, which claims priority from European patent Application 14165492.1 filed 22 Apr. 2014, each of which are hereby incorporated by reference in their entirety.

FIELD OF THE INVENTION

The present invention relates to a process for recovering methane from a gas stream comprising methane and ethylene.

BACKGROUND OF THE INVENTION

It is known to convert methane into saturated and unsaturated, non-aromatic hydrocarbons having 2 or more carbon atoms, including ethylene, by means of a process called "Oxidative Coupling of Methane" (OCM). In this process, a gas stream comprising methane is contacted with an OCM catalyst and with an oxidant, such as oxygen or air. In such a process, two methane molecules are first coupled into one ethane molecule, which is then dehydrogenated into ethylene. Said ethane and ethylene may further react into saturated and unsaturated hydrocarbons having 3 or more carbon atoms, including propane, propylene, butane, butene, etc. Therefore, usually, the gas stream leaving an OCM process contains water, hydrogen, carbon monoxide, carbon dioxide, methane, ethane, ethylene, propane, propylene, butane, butene and saturated and unsaturated hydrocarbons having 5 or more carbon atoms.

In general, the conversion that can be achieved in an OCM process is relatively low. Besides, at a higher conversion, the selectivity decreases so that it is generally desired to keep the conversion low. As a result, a relatively large amount of unconverted methane leaves the OCM process. The proportion of unconverted methane in the OCM product gas stream may be as high as 70 to 80 mol % based on the total molar amount of the gas stream. This unconverted methane has to be recovered from the desired products, such as ethylene and other saturated and unsaturated hydrocarbons having 2 or more carbon atoms, which are also present in such gas streams.

It is known to separate the gas stream leaving an OCM process in the following way. Acid gas (mainly $CO_2$) is removed in two stages, the first stage is an aqueous monoethanolamine (MEA) absorption system, and the second stage removes final traces of $CO_2$ by scrubbing against aqueous NaOH. The $CO_2$-free gas is dried in a dessicant bed and processed in a separation train similar to that used in conventional ethylene plants. The separation sequence comprises a front end demethanizer, deethanizer, C2 splitter, depropanizer, C3 splitter, and a debutanizer. The cryogenic needs for separation are met by a propylene-ethylene cascade refrigeration system that requires ethylene refrigerant only for the demethanization stage.

Thus, it is known to separate methane from saturated and unsaturated hydrocarbons having 2 or more carbon atoms, such as ethylene, by means of cryogenic distillation in so-called "demethanizer" columns. In cryogenic distillation, a relatively high pressure (in general: 23 to 35 bar) and a relatively low (cryogenic) temperature (in general: −120 to −70° C.) are applied to effect the separation of methane. The use of cryogenic distillation following an OCM process is for example disclosed in U.S. Pat. Nos. 5,113,032 and 5,025,108.

An object of the invention is to provide a technically advantageous, efficient and affordable process for recovering methane from a gas stream comprising methane and ethylene, more especially in a case where such gas stream comprises a relatively high proportion of unconverted methane. Such technically advantageous process would preferably result in a lower energy demand and/or lower capital expenditure.

SUMMARY OF THE INVENTION

Surprisingly it was found that such technically advantageous process, resulting in a lower energy demand and/or lower capital expenditure, for recovering methane from a gas stream comprising methane and ethylene may be provided by subjecting such gas stream to the following two steps:

a sorption step which comprises contacting the gas stream comprising methane and ethylene with a sorption agent which has a lower affinity for methane than for ethylene, resulting in sorption of ethylene and 0 to 90% of the methane by the sorption agent and in a gas stream comprising methane in an amount of 10 to 100% based on the amount of methane in the gas stream that is subjected to the sorption step; and a desorption step which comprises desorbing sorbed ethylene and optionally sorbed methane resulting in a gas stream comprising ethylene and optionally methane.

Accordingly, the present invention relates to a process for recovering methane from a gas stream comprising methane and ethylene, comprising:

a sorption step which comprises contacting the gas stream comprising methane and ethylene with a sorption agent which has a lower affinity for methane than for ethylene, resulting in sorption of ethylene and 0 to 90% of the methane by the sorption agent and in a gas stream comprising methane in an amount of 10 to 100% based on the amount of methane in the gas stream that is subjected to the sorption step; and a desorption step which comprises desorbing sorbed ethylene and optionally sorbed methane resulting in a gas stream comprising ethylene and optionally methane.

DETAILED DESCRIPTION OF THE INVENTION

Figure 1:
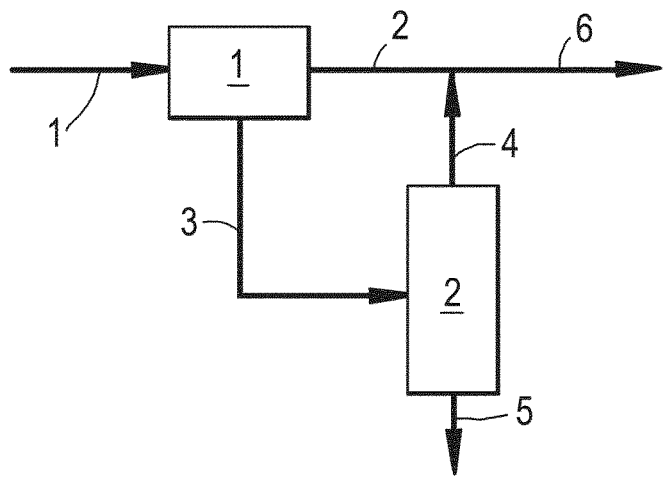
FIG. 1 shows an embodiment of the present invention, in which the sorption step and desorption step of the process of the present invention is followed by a distillation step wherein a gas stream comprising ethylene and methane resulting from said desorption step is distilled.

The gas stream that is subjected to the sorption step of the process of the present invention is a gas stream which comprises methane and ethylene. Preferably, said gas stream originates from the above-mentioned process of oxidative coupling of methane (OCM), wherein a gas stream comprising methane is contacted with an OCM catalyst and with an oxidant, such as oxygen or air, in order to convert the methane into ethylene and optionally ethane and/or saturated and unsaturated, non-aromatic hydrocarbons having 3 or more carbon atoms. Preferably, the gas stream that is subjected to the sorption step comprises 50 to 99 mol % of methane and 1 to 50 mol % of ethylene. Said relative amounts are based on the total amount of the gas stream.

Within the present specification, where reference is made to relative (e.g. molar) amounts of components in a gas stream, such relative amounts are to be selected such that the total amount of said gas stream does not exceed 100%.

In the sorption step of the process of the present invention, a gas stream comprising methane and ethylene is contacted with a sorption agent which has a lower affinity for methane than for ethylene, resulting in sorption of ethylene and optionally methane by the sorption agent and in a gas stream comprising methane. That is to say, the gas stream resulting from the sorption step comprises methane that is not sorbed by the sorption agent. In particular, the amount of methane in the gas stream resulting from the sorption step is 10 to 100%, preferably 30 to 100%, more preferably 40 to 100%, more preferably 50 to 100%, most preferably 60 to 100%, based on the amount of methane in the gas stream that is subjected to the sorption step. The latter percentage may also be referred to as "methane rejection" (methane not being sorbed, but "rejected"). Such "methane rejection" may be varied by varying the pressure and/or the nature of the sorption agent. Consequently, the amount of methane that is sorbed by the sorption agent in the sorption step is 0 to 90%, preferably 0 to 70%, more preferably 0 to 60%, more preferably 0 to 50%, most preferably 0 to 40%, based on the amount of methane in the gas stream that is subjected to the sorption step.

The amount of methane in the gas stream resulting from the sorption step may be at most 100%, or at most 99%, or at most 98%, or at most 95%, or at most 90%, based on the amount of methane in the gas stream that is subjected to the sorption step. Further, the amount of methane in the gas stream resulting from the sorption step may be at least 10%, or at least 30%, or at least 40%, or at least 50%, or at least 60%, based on the amount of methane in the gas stream that is subjected to the sorption step. Thus, said amount of methane in the gas stream resulting from the sorption step may for example be 10 to 99% or 60 to 99%, or 10 to 90% or 60 to 90%. Consequentially, the amount of methane that is sorbed by the sorption agent in the sorption step may be 0%, or at least 1%, or at least 2%, or at least 5%, or at least 10%, based on the amount of methane in the gas stream that is subjected to the sorption step. Further, the amount of methane that is sorbed by the sorption agent in the sorption step may be at most 90%, or at most 70%, or at most 60%, or at most 50%, or at most 40%, based on the amount of methane in the gas stream that is subjected to the sorption step. Thus, said amount of methane that is sorbed by the sorption agent in the sorption step may for example be 1 to 90% or 1 to 40%, or 10 to 90% or 10 to 40%.

In the sorption step of the process of the present invention, a sorption agent is used. In the present specification, "sorption" means a process in which one substance (the sorption agent) takes up or holds or retains another substance by absorption, adsorption or a combination of both.

Further, said sorption agent used in the sorption step of the process of the present invention has a lower affinity for methane than for ethylene. This means that under the conditions applied in said sorption step, including pressure and temperature which are further defined hereinbelow, said sorption agent has a lower affinity for methane than for ethylene. This implies that in the process of the present invention such sorption agent should be used in the sorption step, that the molar ratio of sorbed ethylene to sorbed methane is greater than 1:1, assuming equal partial pressures for ethylene and methane. Preferably, said ratio is in the range of from 1.1:1 to 10:1, more preferably 1.1:1 to 5:1. Sorption agents suitable to be used in the present invention may be selected by comparing the extent of sorption of methane with the extent of sorption of ethylene under any given temperature and pressure conditions for a variety of known sorption agents, assuming equal partial pressures for ethylene and methane. Therefore, a wide range of sorption agents may be used since the only criterion in the present invention is that the sorption agent should have a lower affinity for methane than for ethylene. Without any limitation, examples of suitable sorption agents are activated carbon, zeolite 13X and zeolite 5A.

The pressure in the sorption step of the process of the present invention may vary within wide ranges. Preferably, said pressure is higher than atmospheric pressure. More preferably, said pressure is higher than atmospheric pressure and at most 15 bar, more preferably of from 5 to 15 bar, most preferably 7 to 13 bar.

The temperature in the sorption step of the process of the present invention may also vary within wide ranges. Preferably, said temperature is in the range of from 0 to 100° C., more preferably 10 to 80° C., most preferably 25 to 50° C. Advantageously, in the present invention, said sorption step may be carried out at a non-cryogenic temperature (e.g. of from 0 to 100° C. as mentioned above).

In the desorption step of the process of the present invention, ethylene and optionally methane that are sorbed by the sorption agent are desorbed, resulting in a gas stream comprising ethylene and optionally methane. That is to say, the latter gas stream resulting from the desorption step comprises ethylene and optionally methane that are desorbed from the sorption agent.

Preferably, in the desorption step of the process of the present invention, desorption is effected by reducing the pressure. That is to say, the pressure in the desorption step is lower than the pressure in the sorption step. This is usually referred to as "Pressure Swing Adsorption" (PSA). In the embodiment wherein desorption in the desorption step is effected by reducing the pressure, the pressure in the sorption step is preferably in the range of from 5 to 15 bar, more preferably 7 to 13 bar.

In a case wherein such relatively low pressure (e.g. at most 15 bar) is used in the sorption step, advantageously no or only part of the methane is sorbed in addition to ethylene. Thus, advantageously, in the sorption step of the process of the present invention, a relatively low pressure is applied (e.g. of from 5 to 15 bar as mentioned above). In addition, such low pressure advantageously results in that relatively less compression of the gas stream may be needed. It is especially advantageous that the pressure that may be needed in the sorption step of the process of the present invention may be the same as the pressure in the process from which the gas stream comprising methane and ethylene may originate, such as the pressure in the above-mentioned process of oxidative coupling of methane (OCM). In the latter case, there would be no need at all for any compression of said gas stream in order to carry out said sorption step.

Further, in the embodiment wherein desorption in the desorption step is effected by reducing the pressure, the pressure in the desorption step is preferably in the range of from 0.1 to 3 bar, more preferably 0.5 to 2 bar.

The temperature in the desorption step of the process of the present invention may also vary within wide ranges. Preferably, said temperature is in the range of from 0 to 100° C., more preferably 10 to 80° C., most preferably 25 to 50° C. Advantageously, in the present invention, said desorption step may be carried out at a non-cryogenic temperature (e.g. of from 0 to 100° C. as mentioned above).

Advantageously, the process of the present invention makes it possible to efficiently separate methane from a gas stream comprising methane and ethylene at a relatively low pressure (e.g. at most 15 bar as mentioned above) and at a non-cryogenic temperature (e.g. of from 0 to 100° C. as mentioned above).

Since in the sorption step of the process of the present invention, also part of the methane may be sorbed in addition to ethylene from the gas stream comprising methane and ethylene, in the desorption step also methane may be desorbed, resulting in a gas stream comprising ethylene and methane.

In the embodiment of the process of the present invention, wherein the sorption step results in sorption of ethylene and part of the methane by the sorption agent, preferably, further methane is recovered from the gas stream comprising ethylene and methane resulting from the desorption step. In said embodiment, the process of the present invention comprising the sorption step and desorption step as described above may additionally comprise a distillation step wherein the gas stream resulting from said desorption step is distilled. Said distillation step comprises distilling the gas stream comprising ethylene and methane resulting from the desorption step, said distillation step resulting in a top stream comprising methane and a bottom stream comprising ethylene. Preferably, in said distillation step, the gas stream is distilled at a pressure in the range of from 20 to 40 bar, preferably 23 to 35 bar, and a temperature in the range of from −140 to −50° C., preferably −120 to −70° C. In the present specification, such temperature in a distillation step means the overhead temperature which is the temperature in the condenser at the top of the distillation column.

In said embodiment of the process of the present invention, additionally comprising a distillation step, a distillation column is needed to recover further methane from the gas stream comprising ethylene and methane resulting from the desorption step. This implies that a compressor is also needed in order to increase the pressure of said gas stream (e.g. to 23 to 35 bar as mentioned above) and further that the temperature should be lowered to a cryogenic temperature (e.g. to −120 to −70° C. as mentioned above), so as to enable separation of methane from ethylene in such "demethanizer" distillation column. However, as is demonstrated in the present Examples, it has surprisingly appeared that advantageously the energy demand, especially the demand for compression and refrigeration energy, even for a process comprising said sorption step, said desorption step and said distillation step is significantly lower as compared to a process not comprising said sorption and desorption steps but only comprising said distillation step, in which latter comparative process no methane is removed from the gas stream comprising methane and ethylene before cryogenic distillation. Thus, the present process is a process that, optionally in combination with said distillation step, enables the recovery of methane from a gas stream comprising methane and ethylene in a way that is technically feasible, efficient and affordable since the energy demand is surprisingly lower as compared to the prior art process.

An example of said embodiment of the process of the present invention, comprising an additional distillation step, is schematically shown in FIG. 1. In said FIG. 1, a gas stream 1 comprising methane and ethylene is fed to sorption and desorption unit 1 which comprises a sorption agent which has a lower affinity for methane than for ethylene. The pressure of gas stream 1 is relatively high, for example in the range of from 5 to 15 bar, such that ethylene and 0 to 90% of the methane are sorbed by the sorption agent. A gas stream 2 comprising methane leaves sorption and desorption unit 1, which methane is not sorbed by the sorption agent in sorption and desorption unit 1 and the amount of which methane is 10 to 100% based on the amount of methane in gas stream 1.

After some time, the feed of gas stream 1 to sorption and desorption unit 1 is stopped and the pressure in said unit is reduced. For example, the pressure in sorption and desorption unit 1 may be reduced to a pressure in the range of from 0.1 to 3 bar in a case wherein during the sorption step the pressure is in the range of from 5 to 15 bar, as exemplified above. Through such pressure reduction ethylene and optionally methane that are sorbed by the sorption agent become desorbed. A gas stream 3 comprising ethylene and optionally methane, that are desorbed from the sorption agent, leaves sorption and desorption unit 1, and is then sent to distillation column 2 in case gas stream 3 comprises ethylene and methane.

Once the desorption is completed, the feed of gas stream 1 to sorption and desorption unit 1 is resumed and the above procedure is repeated.

In distillation column 2, a gas stream 3 comprising ethylene and methane is distilled under such pressure and temperature conditions, for example those as described above, that separation between ethylene and methane is effected. That is, a top stream 4 comprising methane and a bottom stream 5 comprising ethylene leave distillation column 2. Finally, top stream 4 comprising methane is combined with gas stream 2 comprising methane resulting in a single stream 6 comprising recovered methane. Said stream 2, stream 4 and/or stream 6, all comprising methane, may advantageously be used (recycled) partially or completely in a process wherein methane is used as a starting material (for further conversion of the recovered methane), for example in the above-mentioned process of oxidative coupling of methane (OCM).

Preferably, the gas stream comprising methane and ethylene that is subjected to the sorption step of the process of the present invention comprises substantially no water. It is also preferred that said gas stream comprising methane and ethylene comprises substantially no hydrogen sulfide.

Within the present specification, by "substantially no" in relation to the amount of a specific component in a gas stream, it is meant an amount which is at most 1,000, preferably at most 500, preferably at most 100, preferably at most 50, more preferably at most 30, more preferably at most 20, and most preferably at most 10 ppmw of the component in question, based on the amount (i.e. weight) of said gas stream.

Further, in an embodiment of the process of the present invention, the gas stream comprising methane and ethylene that is subjected to the sorption step of the process of the present invention additionally comprises components other than said methane and ethylene, such as hydrogen, optionally nitrogen, carbon monoxide, carbon dioxide, ethane and hydrocarbons having 3 or more carbon atoms.

Suitably, said hydrocarbons having 3 or more carbon atoms comprise saturated and unsaturated hydrocarbons having 3 or more carbon atoms, including propane, propylene, butane and butene, and optionally saturated and unsaturated hydrocarbons having 5 or more carbon atoms.

As mentioned above, the gas stream comprising methane and ethylene that is subjected to the sorption step of the process of the present invention may additionally comprise nitrogen. Nitrogen may for example be present in a case where the gas stream originates from an OCM (oxidative coupling of methane) process wherein air is used as oxidant rather than pure oxygen.

In the above-mentioned embodiment of the process of the present invention, wherein the gas stream additionally comprises hydrogen, optionally nitrogen, carbon monoxide, carbon dioxide, ethane and hydrocarbons having 3 or more carbon atoms, said process comprises:

a sorption step which comprises contacting a gas stream comprising methane, ethylene, hydrogen, optionally nitrogen, carbon monoxide, carbon dioxide, ethane and hydrocarbons having 3 or more carbon atoms with a sorption agent which has a lower affinity for methane, hydrogen, nitrogen and carbon monoxide than for carbon dioxide, ethane, ethylene and hydrocarbons having 3 or more carbon atoms, resulting in sorption of hydrocarbons having 3 or more carbon atoms, ethane, ethylene, carbon dioxide and 0 to 90% of the methane by the sorption agent and in a gas stream comprising hydrogen, optionally nitrogen, carbon monoxide and methane wherein the amount of methane in said gas stream is 10 to 100% based on the amount of methane in the gas stream that is subjected to the sorption step; and a desorption step which comprises desorbing sorbed carbon dioxide, ethylene, ethane and hydrocarbons having 3 or more carbon atoms and optionally sorbed methane resulting in a gas stream comprising carbon dioxide, ethylene, ethane, hydrocarbons having 3 or more carbon atoms and optionally methane.

Further, preferably, in the above-mentioned embodiment of the process of the present invention, wherein the gas stream additionally comprises components other than methane and ethylene, the gas stream that is subjected to the sorption step comprises 40 to 90 mol % of methane, 0.5 to 45 mol % of ethylene, 0.01 to 3 mol % of hydrogen, 0 to 80 mol % of nitrogen, 0.1 to 5 mol % of carbon monoxide, 5 to 25 mol % of carbon dioxide, 0.1 to 25 mol % of ethane and 0.5 to 20 mol % of hydrocarbons having 3 or more carbon atoms. Said relative amounts are based on the total amount of the gas stream.

The sorption agents, pressures, temperatures and sorption-desorption method (e.g. PSA) as discussed above also apply to the above-mentioned embodiment of the process of the present invention, wherein the gas stream additionally comprises components other than methane and ethylene.

Preferably, in said embodiment, the process of the present invention additionally comprises a distillation step which comprises distilling the gas stream comprising hydrogen, optionally nitrogen, carbon monoxide and methane resulting from the sorption step, said distillation step resulting in a top stream comprising hydrogen, optionally nitrogen and carbon monoxide and a bottom stream comprising methane. Preferably, in said distillation step, the gas stream is distilled at a pressure in the range of from 20 to 40 bar, preferably 23 to 35 bar, and a temperature in the range of from −170 to −70° C., preferably −150 to −90° C.

In case, in said embodiment, the gas stream comprising hydrogen, optionally nitrogen, carbon monoxide and methane resulting from the sorption step additionally comprises carbon dioxide, said gas stream may be split into a substream that is recycled to the sorption step and a substream that is bled instead of subjecting said gas stream to the above-mentioned distillation step.

Further, preferably, in said embodiment, the process of the present invention additionally comprises a carbon dioxide removal step which comprises removing carbon dioxide from the gas stream comprising carbon dioxide, ethylene, ethane, hydrocarbons having 3 or more carbon atoms and optionally methane resulting from the desorption step, resulting in a gas stream comprising ethylene, ethane, hydrocarbons having 3 or more carbon atoms and optionally methane. In said carbon dioxide removal step, carbon dioxide may be removed by any known method, such as treatment with an amine and then with a caustic agent, such as an aqueous monoethanolamine (MEA) absorption system and aqueous NaOH, respectively, as already mentioned above in the introduction of this specification.

In the embodiment of the process of the present invention, wherein the sorption step results in sorption of hydrocarbons having 3 or more carbon atoms, ethane, ethylene, carbon dioxide and part of the methane by the sorption agent, preferably, further methane is recovered from the gas stream comprising hydrocarbons having 3 or more carbon atoms, ethane, ethylene, carbon dioxide and methane resulting from the desorption step. For example, in said embodiment, further methane may be recovered from the gas stream comprising ethylene, ethane, hydrocarbons having 3 or more carbon atoms and methane resulting from the above-mentioned carbon dioxide removal step. In the latter case, the process of the present invention comprising the sorption step, desorption step and carbon dioxide removal step as described above may additionally comprise a distillation step wherein the gas stream resulting from said carbon dioxide removal step is distilled. Said distillation step comprises distilling the gas stream comprising ethylene, ethane, hydrocarbons having 3 or more carbon atoms and methane resulting from the carbon dioxide removal step, said distillation step resulting in a top stream comprising methane and a bottom stream comprising ethylene, ethane and hydrocarbons having 3 or more carbon atoms. Further, in said distillation step, the gas stream comprising ethylene, ethane, hydrocarbons having 3 or more carbon atoms and methane is preferably distilled at a pressure in the range of from 20 to 40 bar, preferably 23 to 35 bar, and a temperature in the range of from −140 to −50° C., preferably −120 to −70° C.

Further, in said embodiments, the process of the present invention may additionally comprise a distillation step which comprises distilling a gas stream comprising ethylene, ethane and hydrocarbons having 3 or more carbon atoms resulting from the above-mentioned carbon dioxide removal step (in a case wherein the sorption step does not result in sorption of methane) or distilling the above-mentioned bottom stream comprising ethylene, ethane and hydrocarbons having 3 or more carbon atoms resulting from the above-mentioned distillation step (in a case wherein the sorption step results in sorption of part of the methane), said distillation step resulting in a top stream comprising ethylene and a bottom stream comprising ethane and hydrocarbons having 3 or more carbon atoms. Preferably, in said distillation step, said gas stream or said bottom stream, respectively, is distilled at a pressure in the range of from 10 to 40 bar, preferably 13 to 35 bar, and a temperature in the range of from −60 to 40° C., preferably −40 to 20° C.

Alternatively, in said embodiments, the process of the present invention may additionally comprise a distillation step which comprises distilling the above-mentioned streams comprising ethylene, ethane and hydrocarbons having 3 or more carbon atoms, said distillation step resulting in a top stream comprising ethylene and ethane and a bottom stream comprising hydrocarbons having 3 or more carbon atoms. Preferably, in said distillation step, said gas stream or said bottom stream, respectively, is distilled at a pressure in the range of from 10 to 40 bar, preferably 13 to 35 bar, and a temperature in the range of from −60 to 40° C., preferably −40 to 20° C. Further, preferably, in said embodiment, the process of the present invention additionally comprises a distillation step which comprises distilling the above-mentioned top stream comprising ethylene and ethane, said distillation step resulting in a top stream comprising ethylene and a bottom stream comprising ethane. Preferably, in said distillation step, the top stream is distilled at a pressure in the range of from 10 to 40 bar, preferably 13 to 35 bar, and a temperature in the range of from −60 to 40° C., preferably −40 to 20° C.

Figure 2:
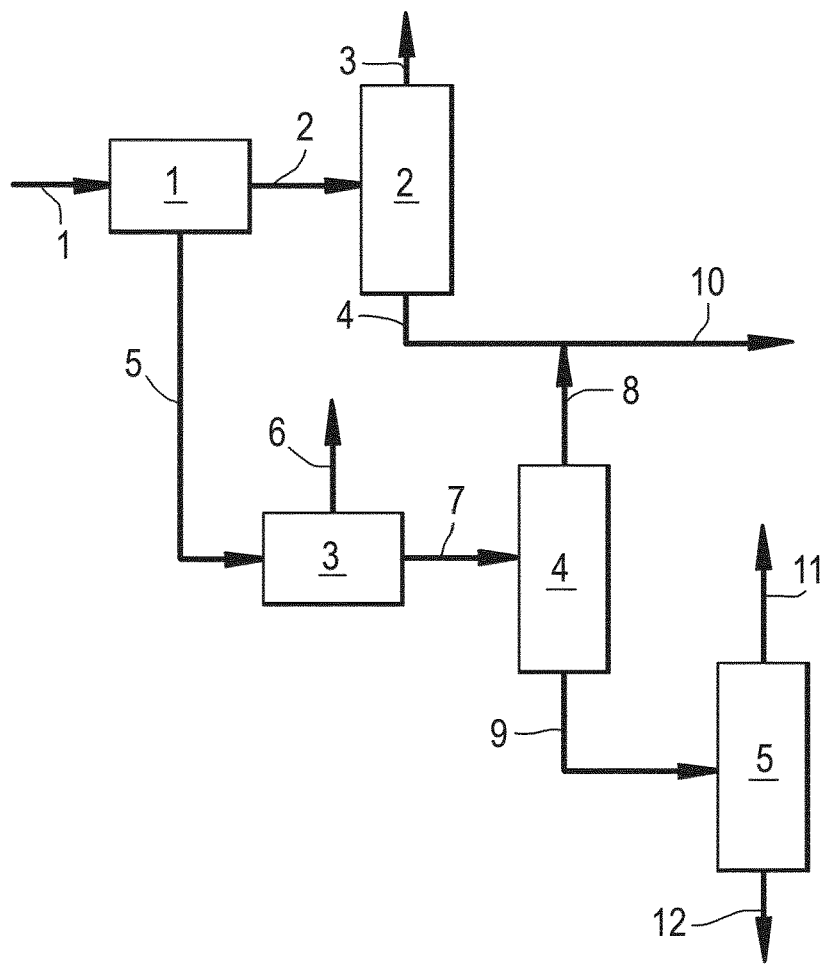
FIG. 2 shows an embodiment of the embodiment shown in FIG. 1, in which the gas stream that is subjected to the sorption step additionally comprises components other than methane and ethylene, namely hydrogen, carbon monoxide, carbon dioxide, ethane and hydrocarbons having 3 or more carbon atoms.

An example of said embodiment of the process of the present invention, wherein the gas stream that is subjected to the sorption step additionally comprises components other than methane and ethylene, namely hydrogen, carbon monoxide, carbon dioxide, ethane and hydrocarbons having 3 or more carbon atoms, is schematically shown in FIG. 2. Hereinafter, the combination of ethylene, ethane and hydrocarbons having 3 or more carbon atoms may also be referred to as hydrocarbons having 2 or more carbon atoms. In said FIG. 2, a gas stream 1 comprising hydrogen, carbon monoxide, carbon dioxide, methane and hydrocarbons having 2 or more carbon atoms is fed to sorption and desorption unit 1 which comprises a sorption agent which has a lower affinity for hydrogen, carbon monoxide and methane than for carbon dioxide and hydrocarbons having 2 or more carbon atoms. The pressure of gas stream 1 is relatively high, for example in the range of from 5 to 15 bar, such that hydrocarbons having 2 or more carbon atoms, carbon dioxide and 0 to 90% of the methane are sorbed by the sorption agent. A gas stream 2 comprising hydrogen, carbon monoxide and methane leaves sorption and desorption unit 1, which hydrogen, carbon monoxide and methane are not sorbed by the sorption agent in sorption and desorption unit 1 and the amount of which methane is 10 to 100% based on the amount of methane in gas stream 1. Gas stream 2 is sent to distillation column 2.

In distillation column 2, gas stream 2 comprising hydrogen, carbon monoxide and methane is distilled under such pressure and temperature conditions, for example those as described above, that separation between on the one hand hydrogen and carbon monoxide and on the other hand methane is effected. That is, a top stream 3 comprising hydrogen and carbon monoxide and a bottom stream 4 comprising methane leave distillation column 2. In case gas stream 2 additionally comprises carbon dioxide, gas stream 2 may be split into a substream that is sent (recycled) to sorption and desorption unit 1 and a substream that is bled (not shown in FIG. 2) instead of sending gas stream 2 to distillation column 2.

After some time, the feed of gas stream 1 to sorption and desorption unit 1 is stopped and the pressure in said unit is reduced. For example, the pressure in sorption and desorption unit 1 may be reduced to a pressure in the range of from 0.1 to 3 bar in a case wherein during the sorption step the pressure is in the range of from 5 to 15 bar, as exemplified above. Through such pressure reduction carbon dioxide, hydrocarbons having 2 or more carbon atoms and optionally methane that are sorbed by the sorption agent become desorbed. A gas stream 5 comprising carbon dioxide, hydrocarbons having 2 or more carbon atoms and optionally methane, that are desorbed from the sorption agent, leaves sorption and desorption unit 1 and is sent to carbon dioxide removal unit 3.

Once the desorption is completed, the feed of gas stream 1 to sorption and desorption unit 1 is resumed and the above procedure is repeated.

In carbon dioxide removal unit 3, carbon dioxide is removed, via stream 6, from gas stream 5 comprising carbon dioxide, hydrocarbons having 2 or more carbon atoms and optionally methane, in a way as exemplified above. A gas stream 7 comprising hydrocarbons having 2 or more carbon atoms and optionally methane leaves carbon dioxide removal unit 3.

In a case where gas stream 7 comprises hydrocarbons having 2 or more carbon atoms and methane, said gas stream is sent to distillation column 4. In distillation column 4, gas stream 7 comprising hydrocarbons having 2 or more carbon atoms and methane is distilled under such pressure and temperature conditions, for example those as described above, that separation between methane and hydrocarbons having 2 or more carbon atoms is effected. That is, a top stream 8 comprising methane and a bottom stream 9 comprising hydrocarbons having 2 or more carbon atoms leave distillation column 4.

Bottom stream 9 comprising hydrocarbons having 2 or more carbon atoms is sent to distillation column 5, wherein it is distilled under such pressure and temperature conditions, for example those as described above, that separation between on the one hand ethylene and on the other hand ethane and hydrocarbons having 3 or more carbon atoms is effected. That is, a top stream 11 comprising ethylene and a bottom stream 12 comprising ethane and hydrocarbons having 3 or more carbon atoms leave distillation column 5.

In a case where gas stream 7 comprises hydrocarbons having 2 or more carbon atoms but no methane, said gas stream is sent directly to distillation column 5 (not shown in FIG. 2), wherein it is also distilled under such pressure and temperature conditions, that separation between on the one hand ethylene and on the other hand ethane and hydrocarbons having 3 or more carbon atoms is effected, as already described above.

Finally, bottom stream 4 comprising methane is combined with top stream 8 comprising methane resulting in a single stream 10 comprising recovered methane. Said stream 4, stream 8 and/or stream 10, all comprising methane, may advantageously be used (recycled) partially or completely in a process wherein methane is used as a starting material (for further conversion of the recovered methane), for example in the above-mentioned process of oxidative coupling of methane (OCM).

The invention is further illustrated by the following Examples.

Examples and Comparative Example

In the Examples exemplifying the invention, the set-up as shown in FIG. 1 is used to recover methane from a gas stream comprising methane and ethylene, said set-up comprising sorption and desorption unit 1 and distillation column 2, as described in the description preceding these Examples, except for one case (the "PSA100" case) wherein distillation column 2 is not used but only sorption and desorption unit 1 is used.

In the Comparative Example exemplifying a prior art process, only said distillation column 2 (and not sorption and desorption unit 1) as shown in FIG. 1 is used to recover methane from a gas stream comprising methane and ethylene.

In the Examples, a gas stream 1 comprising 84.4 wt. % of methane and 15.6 wt. % of ethylene is fed at a temperature of 43° C. and a pressure of 9.8 bar to sorption and desorption unit 1 which comprises a sorption agent which has a lower affinity for methane than for ethylene. The ethylene and part of the methane (in the "PSA60", "PSA75" and "PSA90" cases) or no methane (in the "PSA100" case) from gas stream 1 are sorbed by the sorption agent. A gas stream 2 comprising 99.9+ wt. % of methane leaves sorption and desorption unit 1, which methane is not sorbed by the sorption agent in sorption and desorption unit 1.

The percentage of methane which leaves sorption and desorption unit 1 via gas stream 2 (which methane is not sorbed) is called the "methane rejection" and is based on the amount of methane as fed to sorption and desorption unit 1 via gas stream 1, and is 60, 75, 90 or 100%, respectively, in the "PSA60", "PSA75", "PSA90" and "PSA100" cases, respectively. Gas stream 2 is produced at the same temperature and pressure as gas stream 1 is fed to sorption and desorption unit 1, that is to say 43° C. and 9.8 bar, respectively.

After some time, the feed of gas stream 1 to sorption and desorption unit 1 is stopped and the pressure in said unit is reduced from 9.8 bar to 1 bar, thereby inducing the desorption step of the process of the present invention. The sorbed components (the ethylene and 40, 25, 10 or 0% of the methane from gas stream 1) subsequently become desorbed from the sorption agent and leave sorption and desorption unit 1 via gas stream 3 at a temperature of 23° C. and a pressure of 1 bar. In all of the cases, gas stream 3 is advantageously enriched in ethylene as compared to gas stream 1. In Table 1 below, the composition of gas stream 3 is shown for all cases in the Examples.

TABLE 1

| Gas stream 3 | Methane rejection | Methane (wt. %) | Ethylene (wt. %) |
|---|---|---|---|
| Gas stream 1 | | 84.4 | 15.6 |
| PSA60 | 60% | 68.4 | 31.6 |
| PSA75 | 75% | 57.5 | 42.5 |
| PSA90 | 90% | 35.1 | 64.9 |
| PSA100 | 100% | 0.0 | 100.0 |

Gas stream 3 is then recompressed to 9.8 bar in a first compressor, further compressed to 32.9 bar in a second compressor and finally cooled to −84° C. before it enters distillation column 2 which is a column having 36 theoretical stages. In distillation column 2, the following 2 streams are separated: a top stream comprising 99.9+ wt. % of methane at an (overhead) temperature of −98° C. and a pressure of 31.1 bar (top stream 4) and a bottom stream comprising 99.8+ wt. % of ethylene at a temperature of −5° C. and a pressure of 31.3 bar (bottom stream 5).

In Table 2 below, the reflux ratios and the distillate-to-feed ratios needed to achieve the above separation for the "PSA60", "PSA75" and "PSA90" cases are mentioned. By said "reflux ratio", reference is made to the molar ratio of the molar flow rate of the "reflux stream", which is that part of the stream that leaves the condenser at the top of the distillation column which is sent back to that column, divided by the molar flow rate of the "distillate", which is that part of the stream that leaves the condenser at the top of the distillation column which is not sent back to that column. By said "distillate-to-feed ratio", reference is made to the molar ratio of the molar flow rate of said "distillate" divided by the molar flow rate of the feedstream that is fed to that column (the "feed") which in this case is gas stream 3 having the composition as shown in Table 1 above.

TABLE 2

| | Reflux ratio | Distillate-to-feed ratio |
|---|---|---|
| PSA60 | 0.75 | 0.76 |
| PSA75 | 0.81 | 0.67 |
| PSA90 | 1.11 | 0.46 |

Finally, said top stream 4 comprising methane is combined with gas stream 2 comprising methane resulting in a single stream 6 comprising recovered methane.

As already mentioned above, in the "PSA100" case ("methane rejection" of 100%) in the Examples, distillation column 2 is not used but only sorption and desorption unit 1 is used, since gas stream 3 is advantageously free of methane and requires no further work up. Therefore in this case, the final ethylene and methane streams consist in gas streams 3 and 2, respectively.

As already mentioned above, in the Comparative Example ("base case"), only distillation column 2 (and not sorption and desorption unit 1) as shown in FIG. 1 is used to recover methane from a gas stream comprising methane and ethylene. Said gas stream is the same as gas stream 1, that is to say a gas stream comprising 84.4 wt. % of methane and 15.6 wt. % of ethylene. Further reference is made to the above discussion of characteristics and operation of distillation column 2 which also apply to this Comparative Example. In relation to distillation column 2 as used in this base case, the reflux ratio and the distillate-to-feed ratio are 0.85 and 0.89, respectively.

In Table 3 below, the compression and refrigeration energy needed to recover methane from the gas stream comprising methane and ethylene is included for all of the above-discussed cases, that is to say both the comparative "base case" (Comparative Example) and the cases of the invention which are the "PSA60", "PSA75", "PSA90" and "PSA100" cases (Examples). Said energy is expressed as kilowatt hour ("kWh"; 1 kWh=3.6 megajoules) per kilogram (kg) of ethylene.

TABLE 3

| Case | Configuration | kWh/kg of ethylene |
|---|---|---|
| base case | only distillation (comparative) | 1.77 |
| PSA60 | PSA + distillation | 1.34 |
| PSA75 | PSA + distillation | 1.14 |
| PSA90 | PSA + distillation | 0.91 |
| PSA100 | only PSA | 0.34 |

From Table 3 above, it surprisingly appears that the energy needed to recover methane from the gas stream comprising methane and ethylene is advantageously lowest in case the process of the present invention is carried out. That is, in all of the "PSA60", "PSA75", "PSA90" and "PSA100" cases which exemplify the sorption and desorption process of the present invention, the energy needed to recover said methane, is advantageously lower than the energy needed to effect the same in the "base case" in which latter case such sorption and desorption process is not applied but only a distillation step is performed.

Thus, surprisingly, this advantageous different energy effect obtained with the sorption and desorption process of the present invention, as compared to the prior art process wherein only a distillation step is performed, is even obtained in cases where said sorption and desorption process is followed by a distillation step to recover further methane from gas stream 3, as in the "PSA60", "PSA75" and "PSA90" cases.

That which is claimed is:

1. A process for recovering methane from a gas stream comprising methane and ethylene, comprising:
    a sorption step which comprises contacting the gas stream comprising methane and ethylene with a sorption agent which has a lower affinity for methane than for ethylene, resulting in sorption of ethylene and 0 to 25% of the methane by the sorption agent and in a methane gas stream comprising methane in an amount of 75 to 100% based on the amount of methane in the gas stream that is subjected to the sorption step; and
    a desorption step which comprises desorbing sorbed ethylene and sorbed methane resulting in a gas stream comprising ethylene and methane,
    a distillation step which comprises distilling the gas stream comprising ethylene and methane resulting from the desorption step, said distillation step resulting in a top stream comprising methane and a bottom stream comprising ethylene,
    wherein the gas stream that is subjected to the sorption step is derived from an oxidative coupling of methane process.

2. A process according to claim 1, wherein the gas stream that is subjected to the sorption step comprises of 50 to 99 mol % of methane and 1 to 50 mol % of ethylene.

3. A process according to claim 1, wherein desorption in the desorption step is effected by reducing the pressure.

4. A process according to claim 3, wherein the pressure in the sorption step is in the range of from 5 to 15 bar, and the pressure in the desorption step is in the range of from 0.1 to 3 bar.

5. A process according to claim 1, wherein the gas stream comprising methane and ethylene that is subjected to the sorption step additionally comprises hydrogen, optionally nitrogen, carbon monoxide, carbon dioxide, ethane and hydrocarbons having 3 or more carbon atoms, which process comprises:
    a sorption step which comprises contacting the gas stream comprising methane, ethylene, hydrogen, optionally nitrogen, carbon monoxide, carbon dioxide, ethane and hydrocarbons having 3 or more carbon atoms with a sorption agent which has a lower affinity for methane, hydrogen, nitrogen and carbon monoxide than for carbon dioxide, ethane, ethylene and hydrocarbons having 3 or more carbon atoms, resulting in sorption of hydrocarbons having 3 or more carbon atoms, ethane, ethylene, carbon dioxide and 0 to 25% of the methane by the sorption agent and in a gas stream comprising hydrogen, optionally nitrogen, carbon monoxide and methane wherein the amount of methane in said gas stream is 75 to 100% based on the amount of methane in the gas stream that is subjected to the sorption step; and
    a desorption step which comprises desorbing sorbed carbon dioxide, ethylene, ethane and hydrocarbons having 3 or more carbon atoms and sorbed methane resulting in a gas stream comprising carbon dioxide, ethylene, ethane, hydrocarbons having 3 or more carbon atoms and methane.

6. A process according to claim 5, wherein the gas stream that is subjected to the sorption step comprises 40 to 90 mol % of methane, 0.5 to 45 mol % of ethylene, 0.01 to 3 mol % of hydrogen, 0 to 80 mol % of nitrogen, 0.1 to 5 mol % of carbon monoxide, 5 to 25 mol % of carbon dioxide, 0.1 to 25 mol % of ethane and 0.5 to 20 mol % of hydrocarbons having 3 or more carbon atoms.

7. A process according to claim 5, additionally comprising a distillation step which comprises distilling the gas stream comprising hydrogen, nitrogen, carbon monoxide and methane resulting from the sorption step, said distillation step resulting in a top stream comprising hydrogen, nitrogen and carbon monoxide and a bottom stream comprising methane.

8. A process according to claim 5, additionally comprising a carbon dioxide removal step which comprises removing carbon dioxide from the gas stream comprising carbon dioxide, ethylene, ethane, hydrocarbons having 3 or more carbon atoms and optionally methane resulting from the desorption step, resulting in a gas stream comprising ethylene, ethane, hydrocarbons having 3 or more carbon atoms and methane.

9. A process according to claim 8, wherein the sorption step results in sorption of hydrocarbons having 3 or more carbon atoms, ethane, ethylene, carbon dioxide and part of the methane by the sorption agent, which process additionally comprises a distillation step which comprises distilling the gas stream comprising ethylene, ethane, hydrocarbons having 3 or more carbon atoms and methane resulting from the carbon dioxide removal step, said distillation step resulting in a top stream comprising methane and a bottom stream comprising ethylene, ethane and hydrocarbons having 3 or more carbon atoms.

10. A process according to claim 9, additionally comprising a distillation step which comprises distilling a gas stream comprising ethylene, ethane and hydrocarbons having 3 or more carbon atoms resulting from the carbon dioxide removal step of the process of claim 8 or distilling the bottom stream comprising ethylene, ethane and hydrocarbons having 3 or more carbon atoms resulting from the distillation step of the process of claim 9, said distillation step resulting in a top stream comprising ethylene and a bottom stream comprising ethane and hydrocarbons having 3 or more carbon atoms.

* * * * *